United States Patent
Dacres et al.

(10) Patent No.: US 7,125,482 B2
(45) Date of Patent: Oct. 24, 2006

(54) USE OF ELECTROCHEMISTRY TO DETECT BURIED SERVICE LEAD (PB) AND COPPER (CU) WATER PIPES

(75) Inventors: Chester Malcolm Dacres, Columbia, MD (US); John Marshall, Fallston, MD (US); Dodd V. Ezzard, Flushing, NY (US); Keegan S. Rodkey, Baltimore, MD (US); David G. Deik, Olney, MD (US)

(73) Assignee: Dacco Sci, Inc., Columbia, MD (US)

( * ) Notice: Subject to any disclaimer, the term of this patent is extended or adjusted under 35 U.S.C. 154(b) by 50 days.

(21) Appl. No.: 10/882,194

(22) Filed: Jul. 2, 2004

(65) Prior Publication Data

US 2006/0000724 A1    Jan. 5, 2006

(51) Int. Cl.
*G01N 27/416*    (2006.01)

(52) U.S. Cl. .................. 205/775; 205/790.5; 205/775.5
(58) Field of Classification Search .................. 205/775, 205/776.5, 790.5, 775.5; 324/326, 347, 354, 324/357, 358
See application file for complete search history.

(56) References Cited

U.S. PATENT DOCUMENTS 4,823,072 A * 4/1989 Walcott et al. .............. 205/729

FOREIGN PATENT DOCUMENTS

CA    2299743 A1 * 8/2001

* cited by examiner

*Primary Examiner*—Alex Noguerola

(57) ABSTRACT

The present invention relates to using a rectifier, a groundbed consisting of four (4) copper rods, power supply, three (3) copper/copper sulfate ($Cu/CuSO_4$) reference electrodes, a data logger for detecting and identifying buried lead (Pb) and copper (Cu) service pipes by their electrochemical potentials. More specifically, the present invention relates to using the electrochemical potentials of lead (Pb) versus copper/copper sulfate ($Cu/CuSO_4$) reference electrode (−0.500 volts) and also using the electrochemical potentials of copper versus copper/copper sulfate ($Cu/CuSO_4$) reference electrode (−0.200 volts) which is utilized under field (actual, environmental or in situ) conditions in detecting and differentiating buried lead (Pb) service pipes and buried copper pipes which are sometimes attached to the same water meter and cast iron water supply main.

1 Claim, 3 Drawing Sheets
(1 of 3 Drawing Sheet(s) Filed in Color)

1. Sensing electrode at house connection
2. Datalogger
3. Power supply
4. Rectifier
5. Water meter
6. Sidewalk
7. Sensing electrode at water meter
8. Curb
9. Sensing electrode over watermain
10. Roadway with watermain
11. Groundbed 1. Sensing electrode at house connection
2. Datalogger
3. Power supply
4. Rectifier
5. Water meter
6. Sidewalk
7. Sensing electrode at water meter
8. Curb
9. Sensing electrode over watermain
10. Roadway with watermain
11. Groundbed

USE OF ELECTROCHEMISTRY TO DETECT BURIED SERVICE LEAD (PB) AND COPPER (CU) WATER PIPES

BACKGROUND OF THE INVENTION

1. Field of the Invention

The present invention relates to using electrochemistry for rapid identification of metal alloys which involves the transfer of electron charge across the metal-electrolyte interface. This electrochemical technique is performed by placing a measuring device directly in the electrical circuit creating the electrochemical process. Use of this technique arises from the relative ease of implementation requiring instrumentation that, today, is relatively inexpensive and can be automated.[1] The instrumentation for this invention is comprised of a rectifier, a groundbed consisting of four (4) copper rods, power supply, three (3) copper/copper sulfate ($Cu/CuSO_4$) reference electrodes, a data logger for storing the buried lead and copper service pipes electrochemical potentials. More specifically, the present invention relates to using the electrochemical potentials of lead versus copper/copper sulfate ($Cu/CuSO_4$) reference electrode (−0.500 volts). In addition, the present invention relates to using the electrochemical potentials of copper versus copper/copper sulfate ($Cu/CuSO_4$) reference electrode (−0.200 volts) which is utilized under field (actual, environmental or in situ) conditions in detecting and differentiating buried lead service pipes and buried copper pipes which are sometimes attached to the same water meter and cast iron water supply main.[2]

[1] R. Winston Revie, Uhlig's Corrision Handbook, Wiley, New York, 2000, p. 1179.
[2] A. W. Peabody, Control of Pipeline Corrosion, NACE Press, Houston, Sec. Ed., 2001, p. 4, 301.

2. Prior Art

A major goal in the electrochemical field has long been to detect buried lead and buried copper service water mains in the field without disruption to neighborhood streets. The present technique that is used demands that the streets of busy cities and residential neighborhoods be dug up and the lead and copper service lines are visually identified. These lead and copper service lines are buried three (3) to five (5) feet underground.

The Environmental Protection Agency (EPA) has mandated to several cities within the United States that buried lead service pipes must be identified and replaced within the next five (5) years, in order to prevent lead contamination of the drinking water system. Federal guidelines have set an "action level" for drinking water to contain as much as 15 parts per billion (ppb) of lead. Too much lead in the human body can cause serious damage to the brain, kidneys, nervous system, and red blood cells. It is estimated that lead in drinking water contributes 10% to 20% of total lead exposure in young children. Young children and pregnant women are particularly vulnerable to lead poisoning.

These tight EPA standards require cities to replace underground lead pipes with copper pipes and to implement corrosion control procedures to make water less likely to dissolve lead from pipes and plumbing fixtures. There are about three (3) dozen water systems nationwide whose lead tests have exceeded the federal safety standard since the year 2000, according to data supplied by EPA. Tests in most of these homes have revealed that the high lead content of the drinking water is due to the buried lead service lines. These communities have replaced several of these lines with copper lines in a haphazard manner, which has created the problem of identifying and differentiating the buried lead lines from the copper service lines.

In addition, there are cases where repairs have been done to these underground lead service lines when they fail (leak) due to corrosion. These failed buried lead pipes are dug up, cut, and repaired with copper service lines joining the uncorroded section of the lead line. This presents a electrochemical galvanic corrosion cell which exacerbates the corrosion of the lead pipe and accelerates the amount of lead deposited in the drinking water.[3] The locations of these electrochemical galvanic cells where the lead joins the copper must be identified and the lead portion replaced with copper.

[3] A. W. Peabody, Control of Pipeline Corrosion, NACE Press, Houston, Sec. Ed., 2001, p. 310.

The fundamental relationship in galvanic corrosion is described by Kirchhoff's second law:

$$E_c - E_a = IR_e + IR_m \qquad (1)$$

were are $R_e$ is the resistance of the ground the pipe is buried in, $R_m$ is the resistance of the metallic portion of the galvanic cell, $E_c$ is the polarized potential of the cathodic member (copper), $E_a$ is the polarized potential of the anodic member (lead). Generally, $R_m$ is very small and can be neglected, both $E_a$ and $E_c$ are functions of the galvanic current I; hence, the potential difference between the two (2) metals where there is a current flow through the ground, does not equal the open circuit potential.[4]

[4] R. Winston Revie, Uhlig's Corrosion Handbook, Wiley, New York, 2000, p. 153.

The identification of these lead and copper service mains is extremely important from a health aspect as well as the aesthetic and economical requirements of local governments. This present invention will remove buried lead service lines from the water system. Effectively removing the lead service lines will eliminate the lead content in the drinking water, consequently, improving the health of the population. Another advantage of this invention is that it eliminates the need to dig up the streets and neighborhoods which maintains the existing beauty and condition of the neighborhood. There is a very large economic impact, in that, the savings to local governments would be 80% of their present costs.

Presently, there is no electrochemical method available that would detect and differentiate buried lead and buried copper service water lines without digging up and disrupting a neighborhood. This electrochemical method allows for the identification and differentiation of buried lead and copper service water lines without any disruptions to the neighborhood and no digging up of the buried pipes.

SUMMARY OF THE INVENTION

The principal objective of the present invention is to provide a portable electrochemical instrument comprising of, a rectifier, a data logger, power supply (batteries) and three (3) copper/copper sulfate reference electrodes. This portable instrument is utilized under field (actual, environmental or in situ) conditions to detect the presence of buried lead service water lines and copper service water lines. The detecting of buried lead and buried copper is performed by measuring the electrochemical pipe-to-soil potentials of these metals in the ground. This is a nondestructive procedure, which allows for the accurate detection of these metals by measuring the potentials between them and a reference electrode placed on top of the ground.

The present invention allows for broad applicability, flexibility in utilizing the instrument in various soil environments without having the ability to inspect or evaluate the pipe material of the buried service water line, regardless of the size of the service water line.

The foregoing objectives can be accomplished utilizing the present invention as a portable, nondestructive measuring device providing an in situ instrument, which produces an output potential from the rectifier unto the buried pipeline at the water meter box through the groundbed copper rods and measuring the pipe-to-soil potentials at the sensing reference electrode over the buried service line that goes from the water meter to the water main and simultaneously measuring the pipe-to-soil potentials at the water meter using sensing reference electrode. In addition, the pipe-to-soil potentials from the water meter to the house are measured using a sensing reference electrode over the buried service line.

Four (4) copper grounding rods approximately two (2) feet in length are driven about one (1) foot into the ground around the water meter. These four (4) rods are tied together with stranded electrical cables and ground rod clamps. A connection is made from one of the grounding rods to the rectifier. The rectifier is used to impose a potential on the groundbed into the soil unto the pipes. This process of polarizing the pipe is continued for five (5) minutes and then the decay current is recorded until the various pipe materials are completely depolarized and reside back at their rest potentials. The rest potentials for copper is in the range of −180 mV to −200 mV versus copper/copper sulfate reference electrode, and the rest potential for lead (Pb) is in the range of −500 to −550 mV versus copper/copper sulfate reference electrode. These potentials are used to categorically identify the lead and copper service pipes.

The applied potential made at the groundbed is ramped at a continuous, slow rate of 5 mV per minute relative to the reference electrode using the rectifier. The potential is increased in the anodic direction. The polarization is terminated at a chosen voltage, usually either the passivating potential or some potential active with respect to the passivating potential. The potential at which the polarization is started is usually the potential measured when the polarization process reaches steady state. The identity of the unknown metal can be predicted by the characteristic polarization behavior of the buried underground service lines.[5]

[5] A. Legat and V. Delecek, J. Electrochem. Soc., 142(6), 1851 (1995).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

The preferred embodiment of the invention is a portable, nondestructive testing instrument, comprising of a Portable 10 AMP Rectifier for cathodic protection testing and polarization measurements, two (2) 12 volt automotive batteries used to power the rectifier, Modulogger using HyperWare Version 4.56 software used as a data logger to store the potentials at ten second intervals. The copper/copper sulfate reference electrode is used as a standard for measuring the polarization and depolarization potentials on the buried pipelines.

Figure 1:
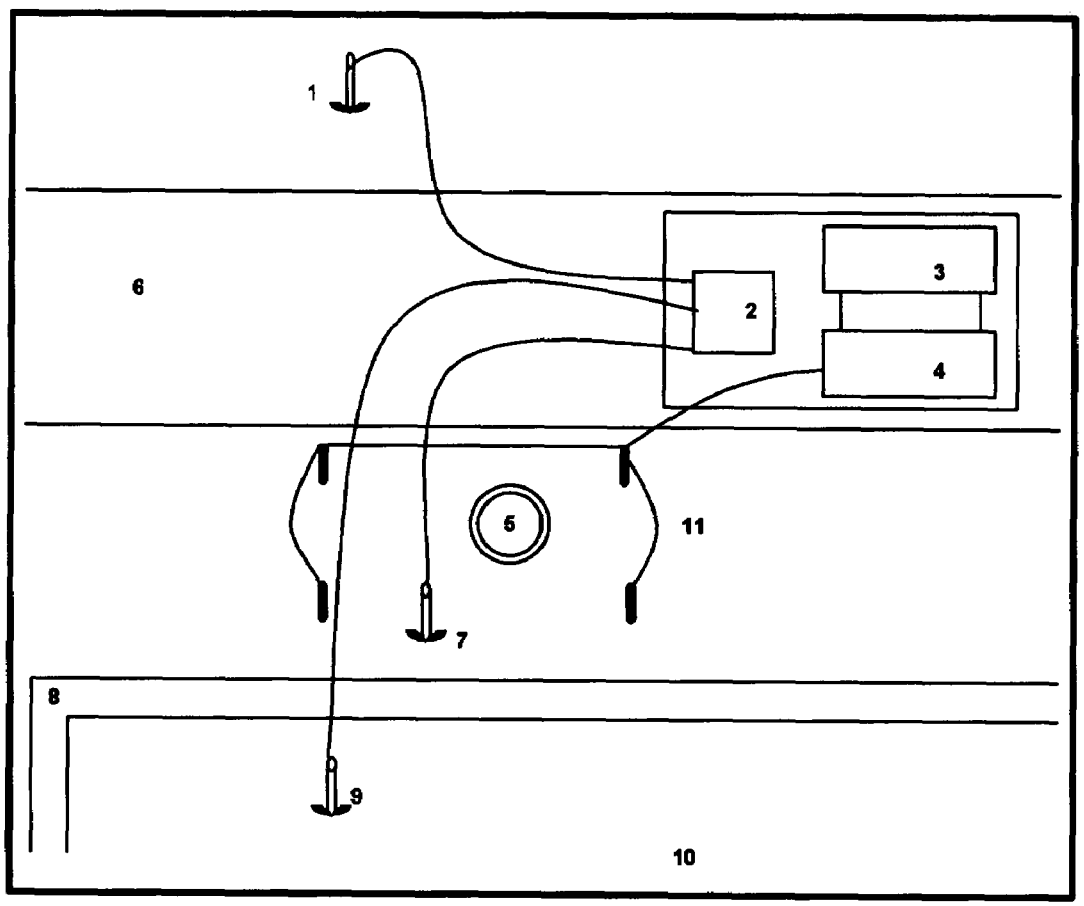
FIG. 1 is a diagram of the set-up of the equipment in-situ.

Referring to the drawing, FIG. 1 is a drawing of the field set-up of the equipment showing the copper/copper sulfate sensing reference electrode at the house connection 1, the copper/copper sulfate sensing reference electrode at the water meter 7, the copper/copper sulfate sensing reference electrode at the water main in the street 9. These sensing reference electrodes all feed into the data logger 2. This figure shows groundbed 11, comprising of four (4) ⅝ inch solid copper rods, two (2) feet in length, and tied together by stranded electrical cable and grounding clamps. This groundbed 11, is tied into the rectifier 4. The power supply 3, is attached to the rectifier.

Figure 2:
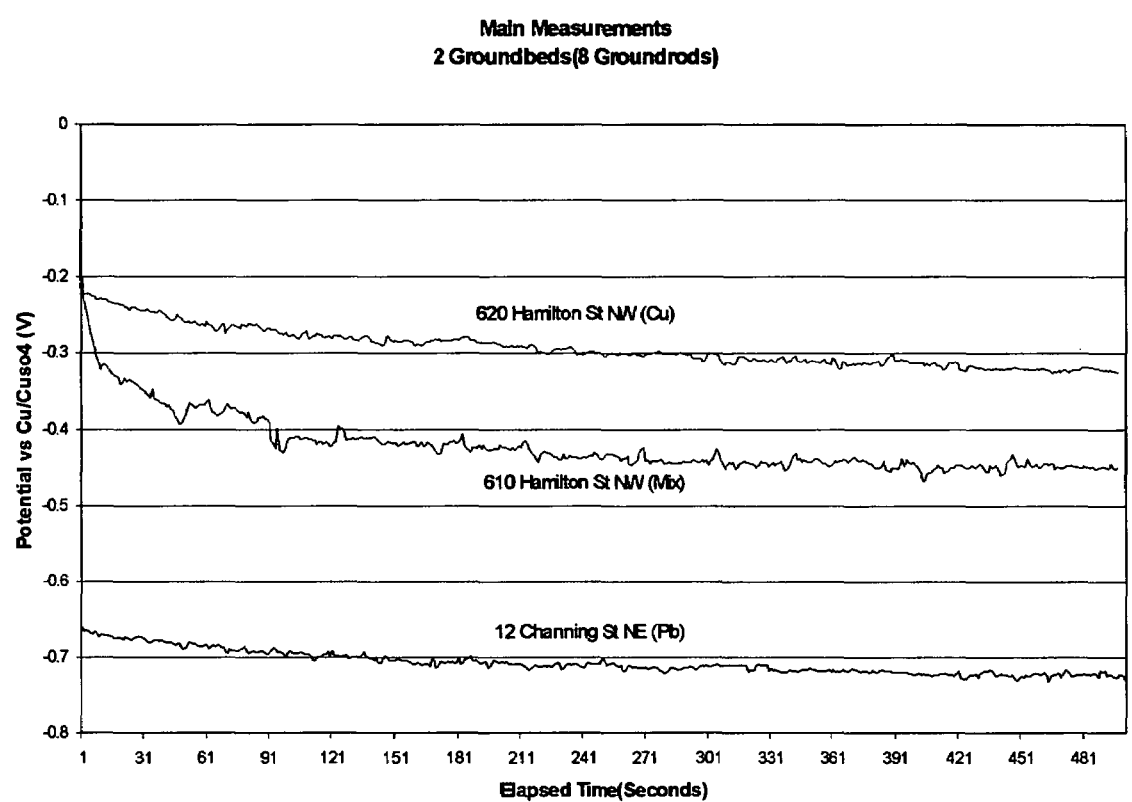
FIG. 2 is an example of the data used to identify the various buried pipe materials.

FIG. 2 is a graphic representation acquired and reduced by the data logger. It shows a distinct plot for copper service line, a distinct plot for a lead service line and a distinct plot for the mix of a copper service line and a lead service line.

Figure 3:
FIG. 3 is a photograph of the equipment in the field.

FIG. 3 is a photograph of the equipment in the field.

We claim:

1. A electrochemical detection method for identifying metallic pipeline materials composed of lead, copper or a lead pipeline joined to a copper pipeline, or in the alternative, a copper pipeline joined to a lead pipeline, when these pipieline material are buried in soil, comprising the steps of:
  (a) providing a portable, set of equipment comprising a rectifier, a data logger, a power supply, and three (3) reference copper/copper sulfate electrodes;
  (b) using the rectifier to polarize a metallic pipeline by imposing a ramped potential on a metallic pipeline buried in soil, wherein the soil acts as an electrolyte, the potential is imposed using an array of metal rods attached to the rectifier to force electrical current into the soil, and the potential is imposed for approximately five (5) minutes to polarize the metallic pipeline;
  (c) interrupting the polarization of the metallic pipeline at a chosen potential and measuring the pipeline potential at its high voltage point and subsequently every ten (10) seconds during the potential decay, the resulting measurements showing a high potential and the metallic pipieline returns to its rest potential value; and
  (d) identifying by a characteristic polarization behavior of the pipeline whether it is a lead pipeline, copper pipeline, or a lead pipeline joined to a copper pipeline, or in the alternative a copper pipeline joined to a lead pipeline.

* * * * *